(12) United States Patent
Parry

(10) Patent No.: US 12,133,632 B2
(45) Date of Patent: *Nov. 5, 2024

(54) ASSESSING FALLOPIAN TUBAL PATENCY

(71) Applicant: Kokopelli Concepts, LLC, Madison, MS (US)

(72) Inventor: John Parry, Ridgeland, MS (US)

(73) Assignee: Kokopelli Concepts, LLC, Madison, MS (US)

( * ) Notice: Subject to any disclaimer, the term of this patent is extended or adjusted under 35 U.S.C. 154(b) by 140 days.

This patent is subject to a terminal disclaimer.

(21) Appl. No.: 18/154,422

(22) Filed: Jan. 13, 2023

(65) Prior Publication Data

US 2023/0147080 A1 May 11, 2023

Related U.S. Application Data

(63) Continuation of application No. 17/100,302, filed on Nov. 20, 2020, now Pat. No. 11,553,835, which is a continuation of application No. 16/248,444, filed on Jan. 15, 2019, now Pat. No. 10,842,363, which is a
(Continued)

(51) Int. Cl.
*A61B 5/00* (2006.01)
*A61B 1/015* (2006.01)
*A61B 1/303* (2006.01)

(52) U.S. Cl.
CPC .............. *A61B 1/015* (2013.01); *A61B 1/303* (2013.01); *A61B 5/4318* (2013.01)

(58) Field of Classification Search
CPC ........ A61B 17/12159; A61B 17/12186; A61B 17/1219; A61B 17/12195; A61B 17/42; A61B 17/43; A61B 17/12099; A61B 17/12022; A61B 17/22102; A61B 17/320758; A61B 17/435
See application file for complete search history.

(56) References Cited

U.S. PATENT DOCUMENTS

| | | |
|---|---|---|
| 5,104,377 A | 4/1992 | Levine |
| 5,259,836 A | 11/1993 | Thurmond et al. |
| 5,935,137 A | 8/1999 | Saadat et al. |

(Continued)

OTHER PUBLICATIONS

Torok et al., "Accuracy of Assessment of Tubal Patency with Selective Pertubation at Office Hysteroscopy Compared with Laparoscopy in Infertile Women", The Journal of Minimally Invasive Gynecology, Sep. 1, 2012, 627-630.

(Continued)

*Primary Examiner* — Brian T Gedeon
(74) *Attorney, Agent, or Firm* — Fish & Richardson P.C.

(57) ABSTRACT

A method of assessing Fallopian tubal patency includes introducing a distension medium into a patient's uterus, introducing a contrasting medium into the uterus, and observing the contrasting medium, for example, via a hysteroscope, to determine whether the contrasting medium flows into one or both Fallopian tubes. A device for assessing Fallopian tubal patency includes a chamber for receiving contrast media, a flow path through the chamber for delivering distension media to a patient's uterus, and a flow controller for regulating the flow of distension media to the patient's uterus. The flow path is configured to permit flow of contrast media from the chamber into the flow path.

4 Claims, 9 Drawing Sheets

Related U.S. Application Data continuation of application No. 15/267,388, filed on Sep. 16, 2016, now Pat. No. 10,456,019.

(60) Provisional application No. 62/220,444, filed on Sep. 18, 2015.

(56) References Cited

U.S. PATENT DOCUMENTS

| | | |
|---|---|---|
| 5,979,446 A | 11/1999 | Loy |
| 5,980,534 A | 11/1999 | Gimpelson |
| 8,052,669 B2 | 11/2011 | Lee-Sepsick et al. |
| 8,550,086 B2 | 10/2013 | Viray et al. |
| 8,551,001 B2 | 10/2013 | Connor et al. |
| 8,585,616 B2 | 11/2013 | Swann et al. |
| 8,695,606 B2 | 4/2014 | Lee-Sepsick et al. |
| 9,907,563 B2 | 3/2018 | Germain et al. |
| 10,070,888 B2 * | 9/2018 | Lee-Sepsick ......... A61M 25/10 |
| 10,456,019 B2 | 10/2019 | Parry |
| 10,842,363 B2 | 11/2020 | Parry |
| 11,553,835 B2 | 1/2023 | Parry |
| 2008/0139923 A1 | 6/2008 | Payne et al. |
| 2009/0171268 A1 | 7/2009 | Williams et al. |
| 2014/0155745 A1 | 6/2014 | Duncan |
| 2015/0133779 A1 | 5/2015 | Yurek et al. |

OTHER PUBLICATIONS

Uchida et al., "Diagnosis of cornual obstruction by transcervical fallopian tube cannulation, Fertility and Sterility", Fertility and Sterility, vol. 50, No. 3, dated Sep. 1988, 434-440.

* cited by examiner

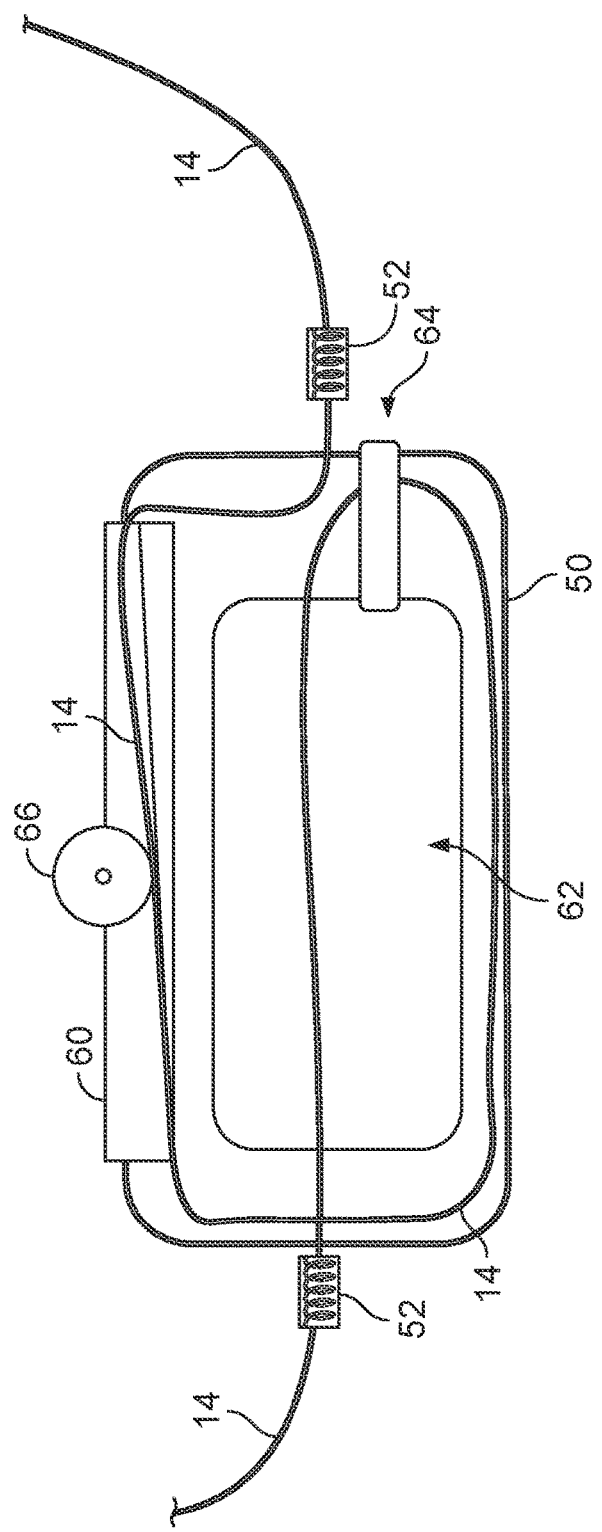
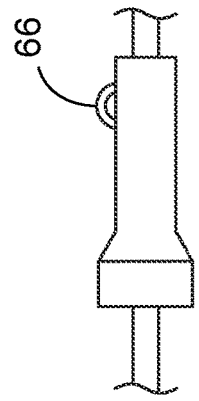
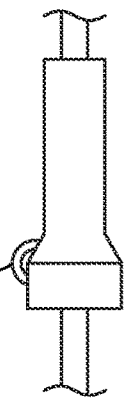
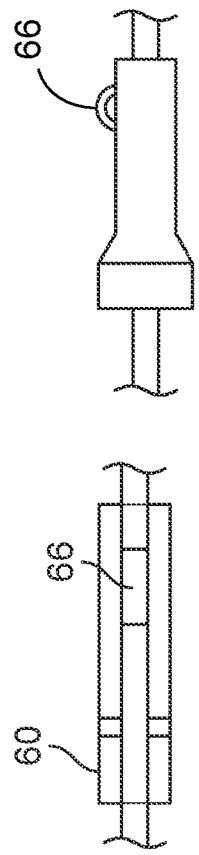
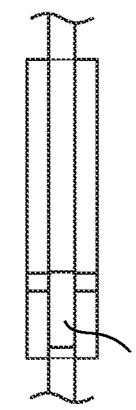
FIG. 6
FIG. 6A
FIG. 6B
FIG. 6C
FIG. 6D

ASSESSING FALLOPIAN TUBAL PATENCY

CROSS-REFERENCE TO RELATED APPLICATIONS

This application is a continuation of U.S. application Ser. No. 17/100,302, filed Nov. 20, 2020, now U.S. Pat. No. 11,553,835, which is a continuation of U.S. application Ser. No. 16/248,444, filed Jan. 15, 2019, now U.S. Pat. No. 10,842,363, issued Nov. 24, 2020, which is a continuation of U.S. application Ser. No. 15/267,388, filed Sep. 16, 2016, now U.S. Pat. No. 10,456,019, issued Oct. 29, 2019, which claims the benefit of U.S. Provisional Application Ser. No. 62/220,444, filed Sep. 18, 2015. All of these prior applications are incorporated by reference in their entirety.

This disclosure relates to methods and devices for hysteroscopically assessing Fallopian tubal patency.

BACKGROUND

Several methods of tubal patency assessment have been previously used. These include hysterosalpingogram, chromopertubation, *chlamydia* antibody testing, and sonosalpingography. In a hysterosalpingogram, an X-ray dye study of the Fallopian tubes is performed. Chromopertubation is performed during laparotomy or laparoscopy, both of which are abdominal surgeries. *Chlamydia* antibody testing is a blood test reflecting risk for tubal disease from previous *chlamydia* infection. Sonosalpingography is an approach that uses ultrasound to observe infusion through a transcervical catheter of a combination of air bubbles in saline or other combinations of fluids with or without air to evaluate the Fallopian tubes. Hysteroscopy has also been used to advance a catheter into the Fallopian tube, with infusion of dye through the catheter. A hysteroscope can also been introduced into the uterus and then after removal of the hysteroscope be followed by ultrasound to see if fluid accumulated in the pelvis during the hysteroscopy without directly observing the process of air or fluid entering or traversing the Fallopian tubes. Falloposcopy has also been used where a camera enters the Fallopian tubes.

SUMMARY

Fallopian tubal patency is assessed by adding air to saline during hysteroscopy. A hysteroscope is advanced past the uterine cervix to look inside the uterus while saline expands the uterine cavity. Air is introduced into the saline and the contrast between the saline and the air allows for visualization as to whether the air bubbles are entering the Fallopian tube, indicating that the Fallopian tube is open, or are remaining in the uterine cavity, indicating that the air bubbles are not able to enter the Fallopian tube. The inability of air bubbles to enter a Fallopian tube can be due to, for example, a closure in the Fallopian tube, a temporary spasm in the Fallopian tube, or other damage to the Fallopian tube. In addition, microscopic patency can exist even if air bubbles are not able to enter the Fallopian tube.

A method of assessing Fallopian tubal patency includes introducing a medium, for example, 0.9% normal saline, into a patient's uterus to distend the uterus; introducing a contrasting medium, for example, air or water insoluble oil, into the distended uterus; and observing the contrasting medium, for example, via a hysteroscope, to determine whether the contrasting medium flows into one or both Fallopian tubes. The method may include introducing the distension medium and/or the contrasting medium via the hysteroscope.

For this technique, in which a camera is advanced past the cervix to observe whether contrasting substances (such as saline and air) pass from the uterus into the Fallopian tubes, syringes, inversion of the drip chamber in IV tubing, and other approaches can be used for introducing contrasting substances. However, because introduction of contrasting substances with one hand can be difficult (as the other hand is holding the hysteroscope), this introduction is often done by an assistant. A device designed to be held and operated by one hand has tubing passing through the device that can be connected with IV tubing and a hysteroscope. The tubing in the device is associated with a flow rate regulator that affects the speed with which substances, for example 0.9% saline, can pass through the tubing. Over a portion of the tubing internal to the device, the tubing is porous so that an additional substance (or substances), for example air, can be introduced into the tubing. The internal chamber (or reservoir) where the additional substance or substances can be introduced into the porous tubing is connected to the outside of the device via a conduit. Substances, for example, air or a water insoluble oil, can be added through this conduit if the contrasting substance is not initially present when the device is made. The use of a water insoluble oil has advantages in instances where there is a need for the contrast medium to sink in saline, for example, for a backward tipped uterus.

A device for assessing Fallopian tubal patency includes a chamber for receiving contrast media; a flow path through the chamber for delivering distension media to a patient's uterus; and a flow controller for regulating the flow of distension media to the patient's uterus. The flow path, for example, tubing passing through the chamber, is configured to permit flow of contrast media from the chamber into the flow path.

Embodiments of this aspect may include one or more of the following features. The tubing is perforated to permit flow of contrast media from the chamber into the tubing. The flow controller is an adjustable clamp. The adjustable clamp is hand controlled. The chamber is configured to be held in an operator's hand. The flow controller is configured to be operated by the same hand holding the chamber for one-handed operation.

BRIEF DESCRIPTION OF THE FIGURES

FIGS. 2 and 2A illustrate a technique of assessing Fallopian tubal patency including the introduction of a contrasting medium into a distension medium of the hysteroscopy set-up;

FIGS. 6-6D are side views of the device illustrating a flow regulating clamp of the device;

DETAILED DESCRIPTION

A flexible hysteroscope, for example, a 2.5 mm flexible pediatric hysteroscope available from Karl Storz (Model 11262BCU1), is used for bubble introduction and visualization. Prior to hysteroscopy, transvaginal ultrasound including antral follicle count can be performed. Tenacula and local anesthesia are typically unnecessary.

Figure 1:
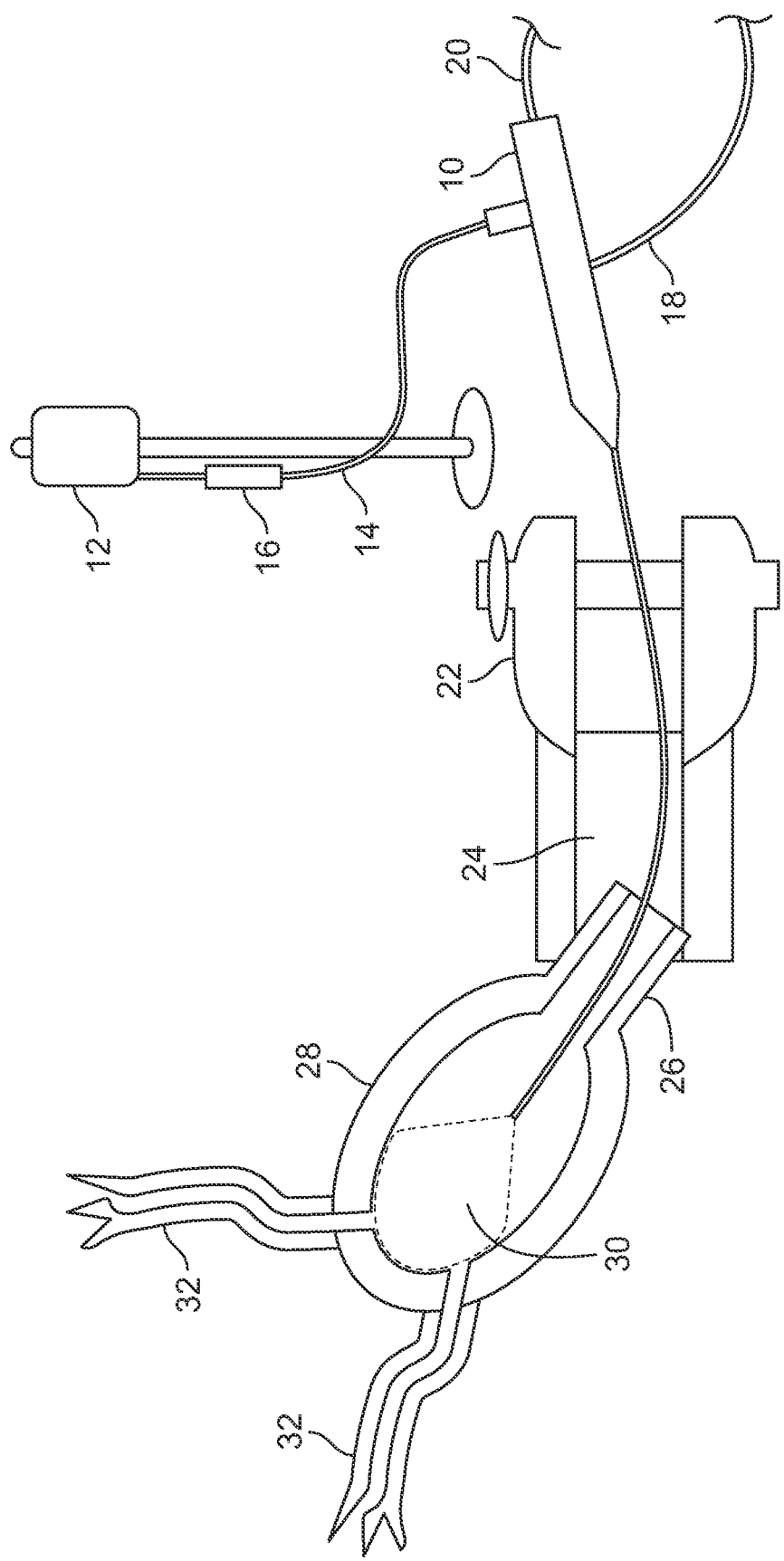
FIG. 1 illustrates a hysteroscopy set-up.

The Parryscope technique for hysteroscopic assessment of Fallopian tubal patency is performed using a hysteroscopy setup. For example, referring to FIG. 1, a hysteroscopy setup includes a hysteroscope 10 coupled to a source of distention medium 12, for example, 0.9% normal saline, via IV tubing 14 and a drip chamber 16. The hysteroscope 10 includes a light source cord 18 and a video cord 20. In use, a speculum 22 is placed in a women's vagina 24 and the hysteroscope 10 is passed through the speculum 22 and the women's cervix 26 into the uterus 28. The typical visible range of the hysteroscope 10 is illustrated by dashed line 30 and includes the entrances to the Fallopian tubes 32.

Figure 2:
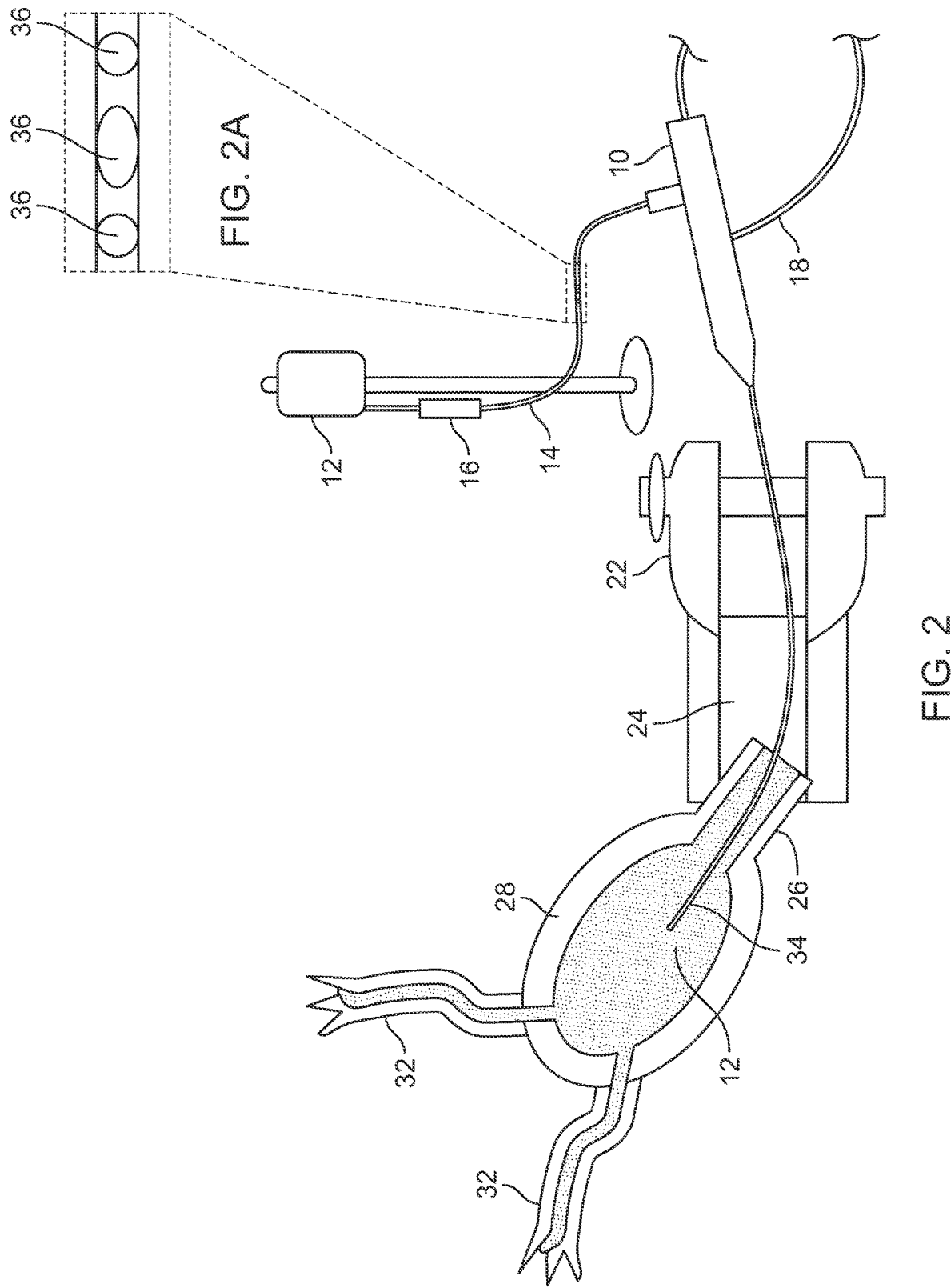
Figure 3:
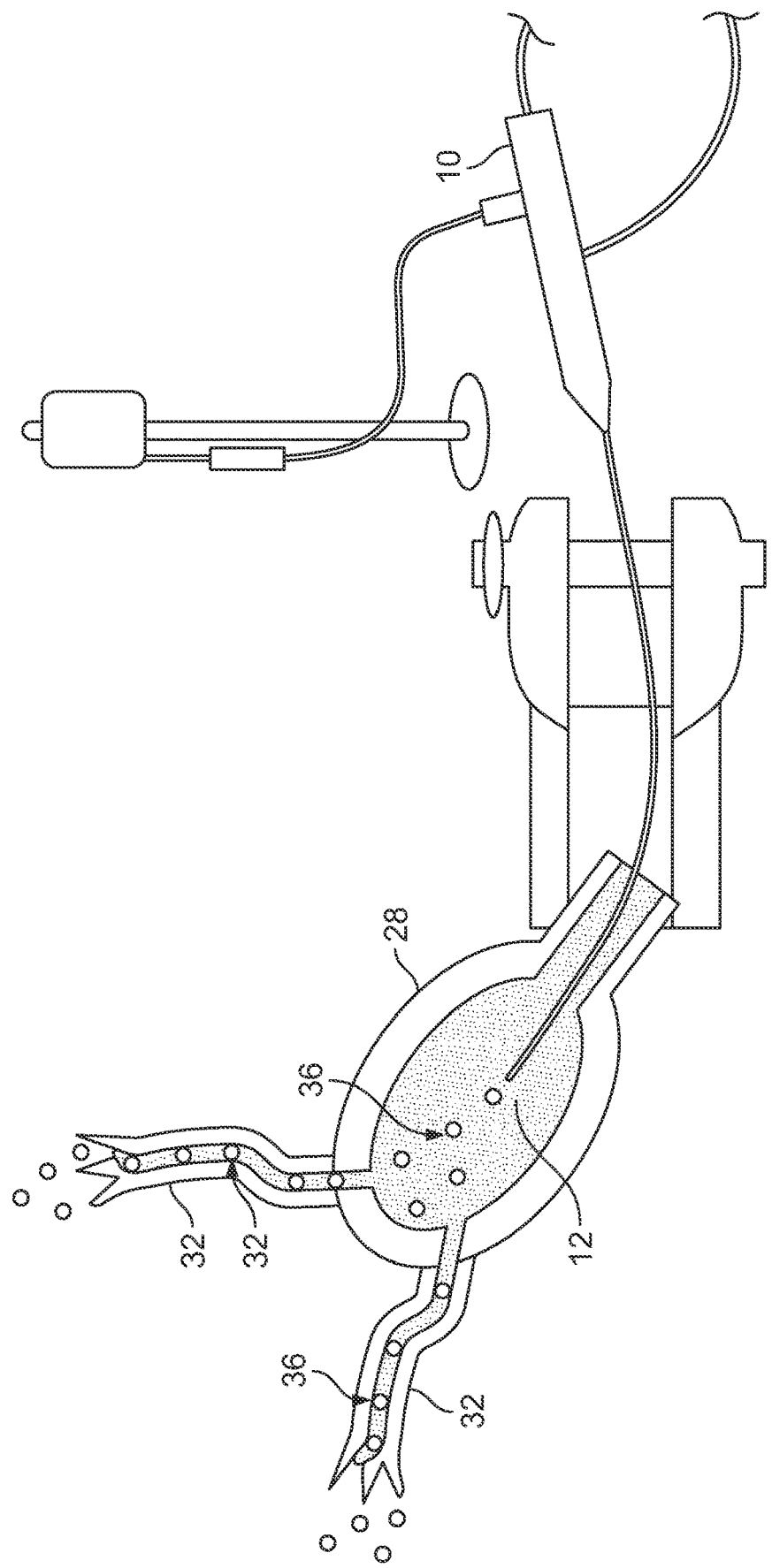
FIG. 3 illustrates the passage of contrasting medium through open Fallopian tubes.
Figure 4:
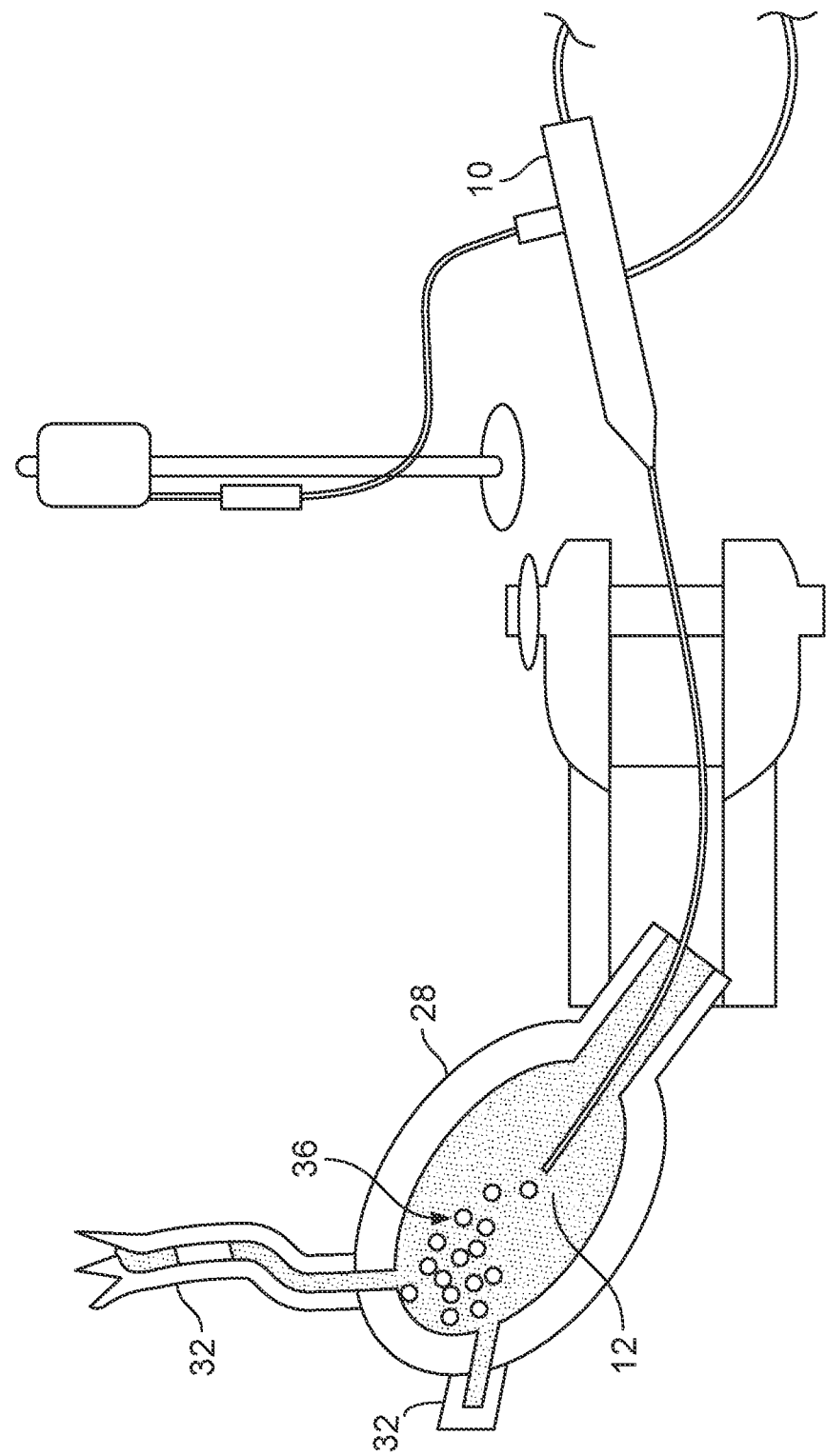
FIG. 4 illustrates contrasting medium blocked from passage due to closed Fallopian tubes.

As illustrated in FIG. 2, after the end 34 of the hysteroscope 10 is advanced past the cervix 26, the operator introduces an appropriate distention medium 12 for hysteroscopy through the hysteroscope into the patient's uterus 28 to distend the uterus, filling the uterus and Fallopian tubes 32 with distention medium 12. If the Fallopian tubes are occluded at their end distal to the uterus, the Fallopian tubes may fill with fluid, but if the tubes are occluded proximal to the uterus, they may not fill with fluid. As the uterus and ostia (the connection between the Fallopian tube and the uterus) are visualized, an amount of air, typically 0.25 milliliters per infusion and preferably less than 2 milliliters for the entire procedure, is then introduced into the uterus by dispersing air bubbles 36 in the IV tubing 14 (FIG. 2A). The air bubbles can be introduced into the IV tubing 14 by, for example, inversion of the drip chamber 16 or syringe injection into the IV tubing 14. The operator then observes, via the hysteroscope, whether the resulting air bubbles flow into one or both Fallopian tubes (FIG. 3) or through neither where the tubes are missing or present but occluded (FIG. 4) to assess whether the Fallopian tubes are open. Air bubbles enter the Fallopian tubes and pass through the Fallopian tubes into the pelvis. Of note, with adequate time to equilibrate for the initial saline infusion, it is unlikely for air bubbles to enter an occluded tube due to the lack of a gradient driving flow through.

An alternative contrasting substance can be used, including one with greater density than saline, which would sink rather than rise. This has value for the retroflexed uterus which "tips backwards."

Prior to introducing the hysteroscope, the operator will typically first place a speculum to visualize the cervix and clean the cervix. Though a vaginoscopic approach can be done, where the hysteroscope is placed in the vagina without a speculum, speculum use allows for the assessment of vaginal disease that might otherwise be harder to visualize. The saline flow rate of the hysteroscope is adjusted for the anticipated cervical dilation and whether the Fallopian tubes are believed open or closed. The more closed the cervix and the more closed the Fallopian tubes, the slower the rate of flow should be. When advancing the hysteroscope through the cervix, the hysteroscope is adjusted for the natural contours on the cervix, and is advanced until the uterine cavity is visualized. If the uterus is poorly distended, the rate of saline infusion may be increased. If the uterus is over distended or the patient is uncomfortable, the rate may be decreased. The uterine cavity is inspected for pathology.

Air bubbles are then introduced, for example, by inversion of the drip chamber on the IV tubing. Typically ¼ of a milliliter of air is all that is required, which translates to an approximately 4 cm column in standard IV tubing. Alternatively, air bubbles can be introduced through a syringe port in the tubing or other approaches. The air bubbles can be flicked in the tubing to create multiple small bubbles instead of one large bubble, but if doing this, a single tiny bubble entering the tubal ostia should not be deemed demonstrative of patency in case the distal tubal fimbria are closed. If air bubbles preferentially congregate towards one side, the patient's hips should be rolled so that the contralateral side is now elevated, causing air bubbles to rise to that side. Additional columns of air bubbles may be added if needed, but two to three columns of air bubbles are typically sufficient and the need for more than six should be rare. If not passing into the tubes, the air bubbles should be observed, such as for 30 to 60 seconds, next to the ostia to exclude the possibility of tubal spasm. After complete assessment of the uterine cavity and evaluation of the bilateral ostia, the hysteroscope is removed, as is the speculum.

The method for assessing patency may exhibit one or more of the following advantages. The technique is gentle with minimal patient discomfort; can be done with low cost for disposable equipment; can be performed in the physician's office; is easy for physicians to learn; uses saline and air, which are unlikely to cause allergic reactions; and does not use X-rays.

The technique can be performed on an awake patient. This enables the patient to deliberately rotate her hips to one side or another, which can help air bubbles reach the ostia (where the Fallopian tubes connect with the uterus), which is important if the position of the uterus makes it hard for air bubbles to reach a particular side. Alternatively, the table can be tilted for an asleep patient. The patient's bladder is preferably completely empty or partially empty to favor air bubbles rising towards her tubal ostia when lying on her back. However, other positions can be used, including but not limited to having a patient with a retroflexed uterus lying on her front.

The technique uses a 2.5 mm or smaller flexible hysteroscope for vaginally nulliparous patients. Though varying sizes can be used, preferably the hysteroscope is smaller than the diameter of the inner cervical lumen to minimize dilation or stretching of the cervix. For patients that have had a previous vaginal delivery, a larger hysteroscope may be appropriate, so as to increase the rate of saline inflow and reduce the rate of saline outflow around the hysteroscope. Although the technique can be performed with a rigid hysteroscope, it is preferred to use a flexible hysteroscope to reduce trauma to the cervix by allowing for easier adjustment to natural contour, as well as to adjust for the anteflexion normal to most uteri with an empty bladder. Fiberoptic, charge-coupled device, and a variety of other types of endoscopic cameras can be used.

The 0.9% normal saline preferred for the method is the same as patients receive intravenously in numerous medical settings and the small amounts used (typically less than 250 mL, some of which will egress through the cervix and not be absorbed) during the procedure are unlikely to cause problems. However, other fluids (for example, Hyskon, glycine, mannitol, and others) could be used. Though air emboli travelling to the lungs are unlikely, the amount of air introduced is less than that typical to sonosalpingography or echocardiograms, which are accepted interventions with rare complications from air infusion. As an alternative to air, other solutions that can be distinguished from the distention media can be used, and multiple permutations involving differing weight, solubility, and color can allow for seeing the contrasting substance pass in to the Fallopian tubes. IV tubing or hanging bags of distention media are not mandatory, as there are multiple other ways of introducing fluid and air, such as by having syringes directly attached to the hysteroscope.

Gases, such as air, are also potential distention medium, with the use of liquids as the contrasting medium. For example, if the uterus is tipped backwards, gas would fill the uterus, and the liquid would enter the Fallopian tubes because the heavier liquid would sink.

Figure 5:
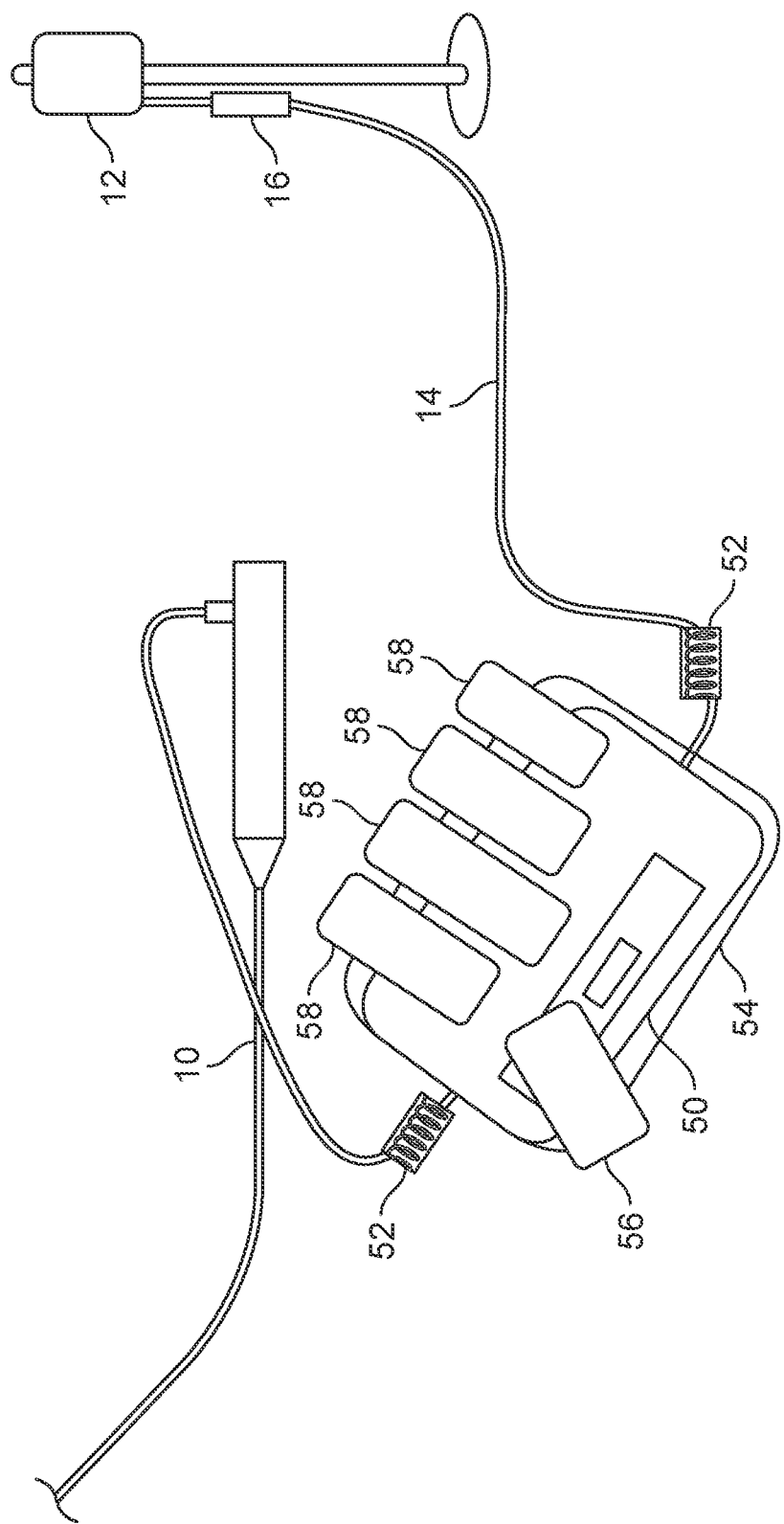
FIG. 5 is a top view of a device for facilitating hysteroscopic assessment of Fallopian tubal patency.

Referring to FIG. 5, a flow regulator 50 for controlling the flow of distention medium 12 and the introduction of bubbles into the distention medium can be connected between the distention medium 12, with or without intervening tubing 14, and the hysteroscope 10. Alternatively, the regulator 50 can be built into the hysteroscope or into a container with the distention medium. Adapters 52, such as Luer or Christmas tree connections, facilitate attachment. The flow regulator 50 is sized and configured to be held in the operator's hand 54, with the operator's thumb 56 and fingers 58 illustrated in FIG. 5. Ergonomic contouring can be present or absent.

Referring to FIG. 6, the flow regulator 50 includes a clamp 60 through which tubing 14 passes, a chamber 62 for holding contrast medium, for example, air, through which tubing 14 also passes, and a channel 64 for the addition of contrast medium to the chamber 62. The distention medium 12 passes through the regulator 50 through the tubing 14. The size of the lumen of the tubing 14 can be selected to provide desired pressure and infusion rate within the uterus, as appropriate for hysteroscopy. Though different flow regulation devices can be used with the flow regulator 50, the flow regulator clamp 60 illustrated in FIGS. 6-6D includes a wheel 66, which is rolled upwards or downwards with variable degrees of tubing compression so as to determine the speed through which the distention medium passes through the flow regulator 50. The clamp 60 is shown in the closed position in FIGS. 6A and 6B and in the fully open position in FIGS. 6C and 6D. Alternatives to the clamp 60 include a flow regulator valve or a design in which the walls of the chamber 62 act to regulate flow through the tubing 14 by restricting the tubing 14 as the tubing passes through the walls, the restriction of the tubing 14 being alleviated by pressure exerted on the chamber by the operator squeezing the chamber, allowing for increased flow.

The contrasting medium chamber 62 surrounds a portion of the tubing 14. The chamber 62 can be incorporated in various ways into the flow regulator 50, such as before or after the flow regulator clamp 60, and the chamber 62 can have a volume of, for example, about 10-50 mL. Porousness of the tubing 14 within the chamber 62 allows the addition of the contrasting medium into the tubing 14 so that the contrasting medium is present with the distention medium. The tubing diameter and lumen size and the number of sites for porousness can be varied. For example, if saline is the distention medium and air is the contrasting medium, depending on the porousness selected, the regulator 50 would generate a few large air bubbles or many small air bubbles.

Figures 7, 7A:
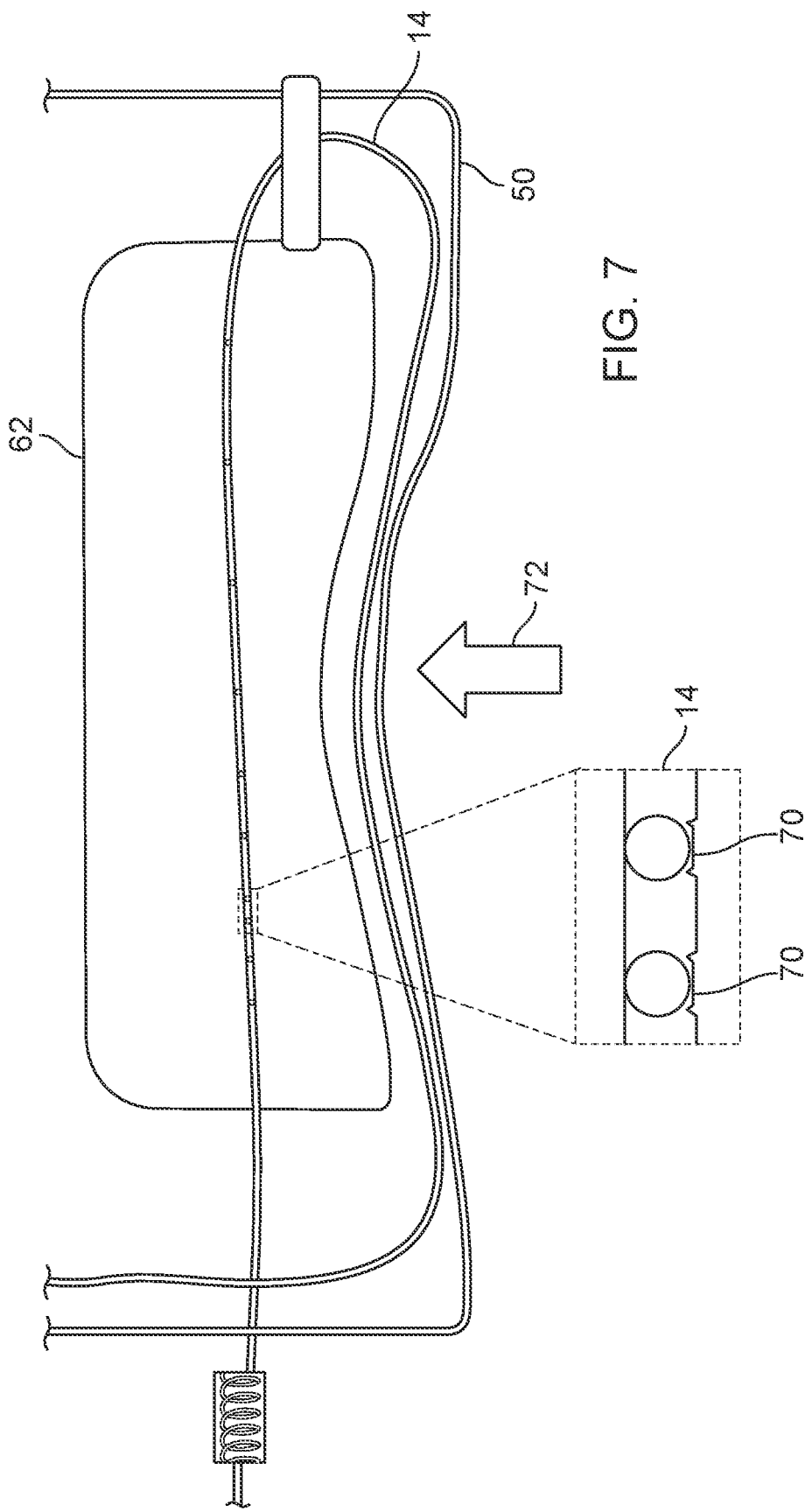
FIGS. 7 and 7A illustrate the introduction of contrast medium into the distension medium.

As illustrated in FIGS. 7 and 7A, the porous tubing 14 located within the chamber 62 can define channels 70 that allow entry of contrast medium when opened through pressure. To force the contrasting medium into the tubing 14, in one example, the operator squeezes the flow regulator 50, arrow 72, increasing the pressure in the chamber 62, pushing the contrasting medium across the porous region of the tubing 14 into the tubing 14. The combined distention and contrast medium then advance briefly through the tubing 14 before releasing pressure.

Figure 8:
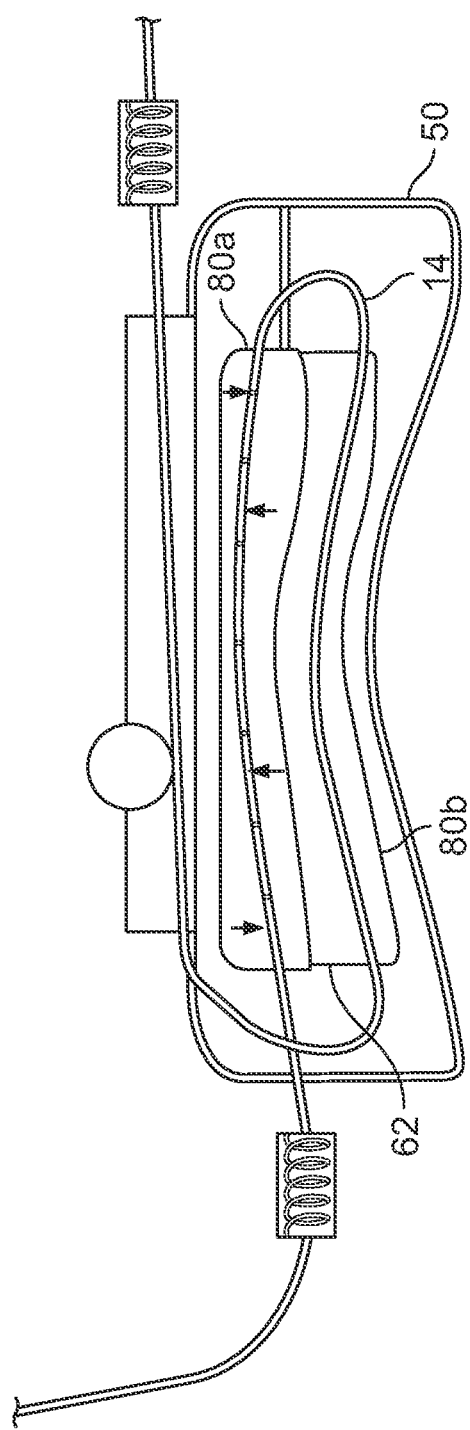
FIGS. 8 and 8A are side views of a dual chamber embodiment of the device.
Figure 8A:
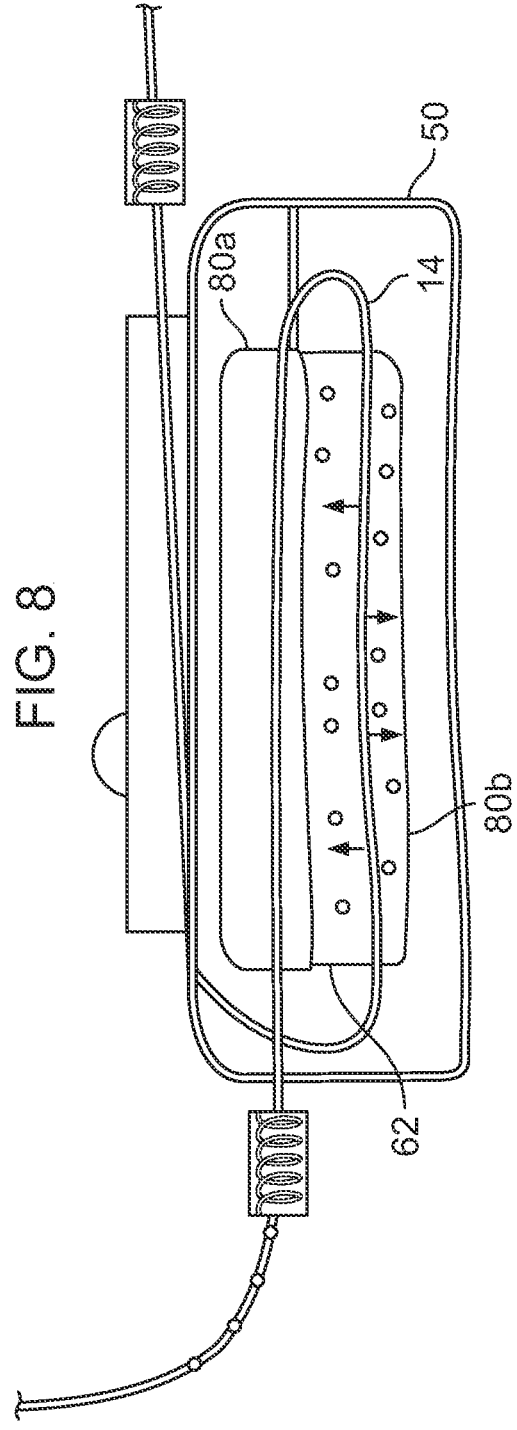

The release of pressure in the embodiment of FIG. 7 draws distention medium in the reverse direction into the contrast medium chamber 62. Referring to FIGS. 8 and 8A, to avoid mixing of the mediums within the chamber 62, a unidirectional porous tubing can be used, which allows contrast medium to enter the tubing 14 with pressure, with displacement of distention medium into a separate chamber with release of pressure. The contrasting medium chamber 62 includes two separate chambers 80a, 80b. The portion of tubing 14 in the first chamber 80a allows contrast medium to enter the tubing from the chamber 80a when pressure is applied to the chamber 62 (FIG. 8), and the portion of tubing 14 in the second chamber 80b allows contrast medium to exit the tubing into the chamber 80b when pressure is released (FIG. 8A).

Figure 9:
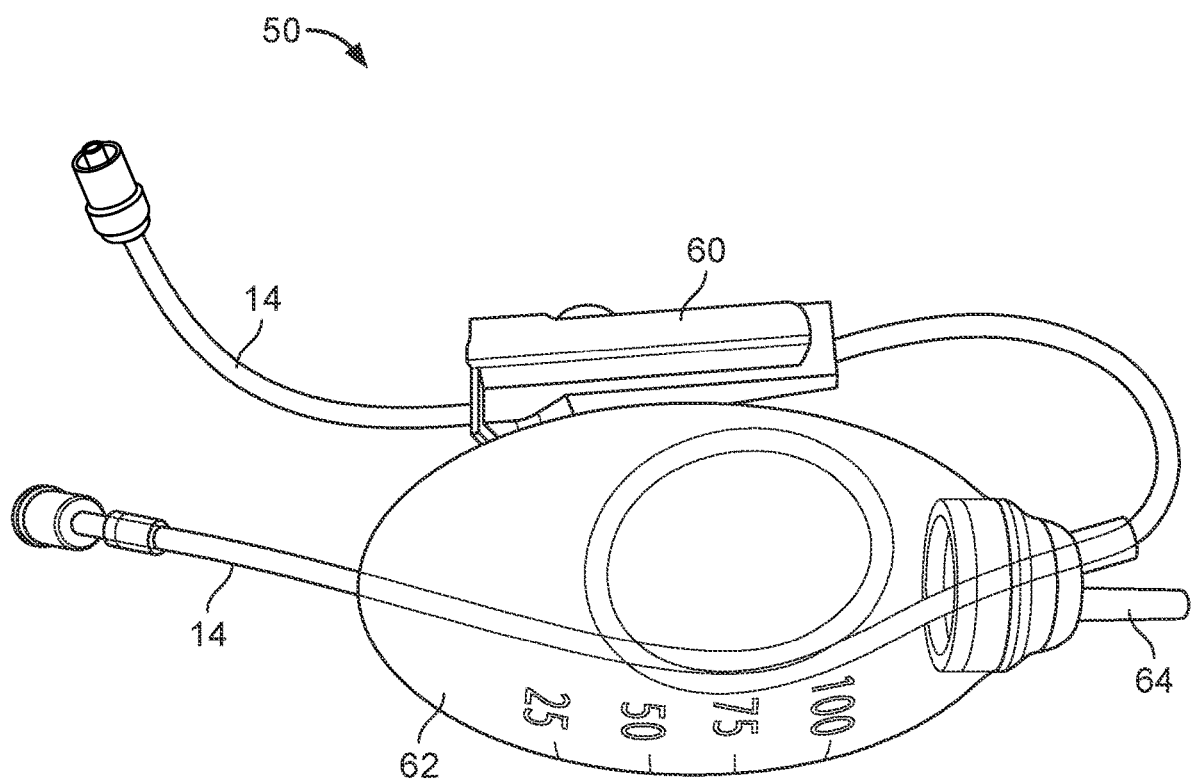
FIG. 9 illustrates a single chamber embodiment of the device.

FIG. 9 illustrates a flow regulator 50 for assisting in hysteroscopic assessment of Fallopian tubal patency having a single contrast medium chamber 62 and a clamp 60 external to the chamber 62. The clamp 60 can be located upstream or downstream of the chamber 62, though by positioning the clamp 60 downstream of the chamber 62, squeezing the chamber so that contrasting medium enters the tubing 14 does not have a significant effect on the pressure experienced by the patient. Chamber 62 can be constructed, for example, of silicone, and, in the illustrated embodiment has a volume of 150 mL for contrast medium, though smaller or larger volumes can be used. For example, the chamber 62 can be a Silicone Evacuator available from Medline Industries, Inc., Ref #DYNME1305. The tubing 14 for flow of distention medium can be constructed of, for example, silicone having, for example, an inner diameter (lumen) of about 3.2 mm and an outer diameter of about 6.4 mm, a porosity of one millimeter with six points of fenestration, and can be straight or include a loop or loops inside the chamber 62. The loop or loops increases the length of the tubing within the chamber to spread out the porosity, increasing the spacing between air bubbles within the distention medium.

What is claimed is:

1. A method of assessing Fallopian tubal patency, comprising:
   directly coupling an inflow connector to a port of a 2.5 mm or smaller hysteroscope;
   introducing a distention medium through the inflow connector to the hysteroscope and into a patient's uterus to distend the uterus;
   introducing a total of less than 2 milliliters of contrasting medium through the inflow connector to the hysteroscope and into the distended uterus, the contrasting medium flowing into the uterus at a location spaced from both ostia; and
   observing the contrasting medium via the hysteroscope to determine whether the contrasting medium flows into a Fallopian tube.

2. The method of claim 1 wherein the distention medium comprises saline.

3. The method of claim 1 wherein the contrasting medium comprises air.

4. The method of claim 1 wherein the contrasting medium comprises water insoluble oil.

\* \* \* \* \*